United States Patent
Docherty et al.

(10) Patent No.: US 11,694,109 B2
(45) Date of Patent: Jul. 4, 2023

(54) DATA PROCESSING APPARATUS FOR ACCESSING SHARED MEMORY IN PROCESSING STRUCTURED DATA FOR MODIFYING A PARAMETER VECTOR DATA STRUCTURE

(71) Applicant: ODH, Inc., Princeton, NJ (US)

(72) Inventors: John Docherty, Princeton, NJ (US); David Kho, Princeton, NJ (US); Adam Johnson, Princeton, NJ (US); Ayan Chadhuri, Princeton, NJ (US)

(73) Assignee: ODH, INC., Princeton, NJ (US)

(*) Notice: Subject to any disclaimer, the term of this patent is extended or adjusted under 35 U.S.C. 154(b) by 492 days.

(21) Appl. No.: 15/999,153

(22) Filed: Aug. 16, 2018

(65) Prior Publication Data
US 2019/0057284 A1     Feb. 21, 2019

Related U.S. Application Data

(60) Provisional application No. 62/546,528, filed on Aug. 16, 2017.

(51) Int. Cl.
*G06K 9/62*       (2022.01)
*G06N 20/00*     (2019.01)
(Continued)

(52) U.S. Cl.
CPC .............. *G06N 20/00* (2019.01); *G06F 16/24* (2019.01); *G06F 18/217* (2023.01);
(Continued)

(58) Field of Classification Search
None
See application file for complete search history.

(56) References Cited

U.S. PATENT DOCUMENTS

| | | | |
|---|---|---|---|
| 9,348,735 B1 * | 5/2016 | Cohen | G06F 11/34 |
| 2003/0018595 A1 | 1/2003 | Chen et al. | |
| (Continued) | | | |

OTHER PUBLICATIONS

International Search Report and Written Opinion in Appln. No. PCT/US2018/000324, dated Feb. 1, 2019, 12 pages.

(Continued)

*Primary Examiner* — Peet Dhillon
(74) *Attorney, Agent, or Firm* — Pillsbury Winthrop Shaw Pittman LLP

(57) ABSTRACT

Methods, systems, and apparatus for training model parameters stored in shared memory to predict risk. The method may include obtaining training data that includes a plurality of training data structures that each represent attributes of an entity, wherein each training data structure represents (i) features derived from a first set of categories defined by a first model and from a second set of categories defined by a second model, and (ii) a risk-level associated with the entity. For each respective training data structure, providing the training data structure as an input to the model, receiving an output from the model based on the model's processing of the training data structure, determining an amount of error between the output of the model and the risk-level of the training data structure, and adjusting a parameter value of the model stored in a shared memory based on the determined error.

23 Claims, 6 Drawing Sheets

(51) Int. Cl.
*G16H 40/20* (2018.01)
*G06F 18/21* (2023.01)
*G06F 18/214* (2023.01)
*G16H 10/60* (2018.01)
*G16H 15/00* (2018.01)
*G06F 16/24* (2019.01)
*G06N 5/04* (2023.01)

(52) U.S. Cl.
CPC ......... *G06F 18/2148* (2023.01); *G16H 10/60* (2018.01); *G16H 15/00* (2018.01); *G16H 40/20* (2018.01); *G06N 5/04* (2013.01)

(56) References Cited

U.S. PATENT DOCUMENTS

| | | | |
|---|---|---|---|
| 2008/0081955 A1* | 4/2008 | Eisenhandler | G06Q 10/06315 600/300 |
| 2008/0162385 A1* | 7/2008 | Madani | G06N 20/00 706/12 |
| 2011/0119212 A1* | 5/2011 | De Bruin | A61B 5/00 706/12 |
| 2016/0125316 A1 | 5/2016 | Kadav et al. | |
| 2016/0232321 A1* | 8/2016 | Silverman | G16H 50/50 |
| 2017/0140114 A1* | 5/2017 | Are | G16H 50/20 |
| 2017/0169358 A1 | 6/2017 | Choi et al. | |
| 2017/0286622 A1* | 10/2017 | Cox | G16H 50/30 |
| 2018/0060509 A1* | 3/2018 | Tekumalla | G16H 50/20 |

OTHER PUBLICATIONS

PCT International Preliminary Report on Patentability in Appln. No. PCT/US2018/000324, dated Feb. 18, 2020, 11 pages.

* cited by examiner

DATA PROCESSING APPARATUS FOR ACCESSING SHARED MEMORY IN PROCESSING STRUCTURED DATA FOR MODIFYING A PARAMETER VECTOR DATA STRUCTURE

CROSS-REFERENCE TO RELATED APPLICATION

This application claims the benefit of U.S. Provisional Patent Application No. 62/546,528, filed Aug. 16, 2017, the entire contents of which are herein incorporated by reference.

TECHNICAL FIELD

This specification is directed to the field of data processing. Specifically, this application relates to the accessing of a shared memory for modifying a parameter vector data structures and then used to train a machine learning model.

BACKGROUND

A machine learning model may be configured to analyze labeled training data and then draw inferences from the training data. Once the machine learning model has been trained, sets of data that are not labeled may be provided to the machine learning model as an input. The machine learning model may process the input data and make predictions about the input based on inferences learned during training.

SUMMARY

According to one innovative aspect of the present disclosure, a data processing apparatus for accessing shared memory in processing structured data for modifying a parameter vector data structure is disclosed. The data processing apparatus may include an input port or device for receiving a plurality of data structures, with each data structure including fields storing respective values of respective attributes of an entity, wherein values of at least a plurality of the fields represent (i) a plurality of features that are derived from a first set of categories defined by a first model and from a second set of categories defined by a second model, and (ii) a risk-level associated with the entity, a shared memory that stores a parameter vector data structure of a machine learning model, an executable logic engine that, for each received data structure: provides the data structure as an input to the machine learning model; and receives an output data structure from the machine learning model based on the machine learning model's processing of the data structure, and a parameter vector adjustment engine that: parses the data structure input into the machine learning model by the executable logic engine to identify a field storing a first value representing a risk level, parses the output data structure generated by the machine learning model based on the machine learning model's processing of the input data structure to identify a field in the output data structure storing a second value representing an output risk-level output from the machine learning model, determines an amount of error between the second value output from the machine learning model and the first value of the risk-level of the data structure, and accesses, from the shared memory, an entry in the parameter vector data structure of the machine learning model that stores one or more parameters of the machine learning model, and adjusts the one or more parameter values of the machine learning model based on the determined amount of error.

Other versions include corresponding systems, apparatus, methods, and computer programs, configured to perform the actions of the operations described above. In some implementations, the operations may be instructions that are encoded on a computer storage device.

These and other versions may each optionally include one or more of the following features. For instance, in some implementations, the first set of categories defined by the first model may include categories related to physical health of an entity.

In some implementations, the second set of categories defined by the second model may include categories related to behavioral health of an entity.

In some implementations, the risk-level associated with the entity may represent a historical cost associated with the entity.

According to another innovative aspect of the present disclosure, a method performed by a data processing apparatus for training a machine learning model to improve the machine learning model's capability to predict a risk-level associated with an entity is disclosed. The method may include actions of obtaining a set of training data that includes a plurality of training data structures that each represents attributes of an entity, wherein each training data structure in the set of training data structures represents (i) a plurality of features that are derived from a first set of categories defined by a first model and from a second set of categories defined by a second model, and (ii) a risk-level associated with the entity, and for each respective training data structure of the plurality of training data structures: providing the training data structure as an input to the machine learning model, receiving an output from the machine learning model based on the machine learning model's processing of the training data structure, determining an amount of error between the output of the machine learning model and the risk-level of the training data structure, and adjusting one or more parameter values of the machine learning model based on the determined error.

Other versions include corresponding systems, apparatus, methods, and computer programs, configured to perform the actions of the operations described above. In some implementations, the operations may be instructions that are encoded on a computer storage device.

These and other versions may each optionally include one or more of the following features. For instance, in some implementations, one or more of the features of the training data structure may represent a diagnostic code.

In some implementations, one or more of the features of the training data structure may represent a pharmacy code.

In some implementations, one or more of the features of the training data structure may represent demographic information of the entity.

In some implementations, the first set of categories defined by the first model may include categories related to physical health of an entity.

In some implementations, the second set of categories defined by the second model may include categories related to behavioral health of an entity.

In some implementations, the risk-level associated with the entity may represent a historical cost associated with the entity.

In some implementations, a first feature of the plurality of features may be assigned a first value if an attribute of the entity can be mapped to the category from which the feature is derived.

In some implementations, a second feature of the plurality of features may be assigned a second value that is different from the first value if an attribute of the entity cannot be mapped to the category from which the feature is derived.

According to another innovative aspect of the present disclosure, a data processing apparatus for accessing shared memory in processing data records for generating an item of structured training data is disclosed. The data processing apparatus may include an input port for receiving, from one or more databases, data records, each representing a profile of attributes related to an entity, a shared memory that stores the received data records, a segmentation engine that accesses, from the shared memory, one or more of the data records and that processes the one or more of the data records and, based on the processing, segments data representing an obtained profile of attributes into distinct sets of risk-scoring components, with the segmenting based on a risk-type that is associated with each respective attribute, wherein the distinct sets of risk-scoring components include at least a first set of risk-scoring components and a second set of risk-scoring components, and wherein each respective attribute is segmented into only one of the first set of risk-scoring components or the second set of risk-scoring components, and an executable logic engine that: maps each of the risk-scoring components of the first set of risk-scoring components to one or more categories of a first plurality of categories, maps each of the risk-scoring components of the second set of risk-scoring components to one or more categories of a second plurality of categories, and generates a structured item of data item based on (i) the mapping of the first set of risk-scoring components, and (ii) the mapping of the second set of risk-scoring components, with the structured item of data including at least a first field specifying a numerical value indicating that one of the risk-scoring components of the first set of risk scoring components maps to a particular category of the first plurality of categories and at least a second field specifying a numerical value indicating that one of the risk-scoring components of the second set of risk-scoring components maps to a particular category of the second plurality of categories.

Other versions include corresponding systems, apparatus, methods, and computer programs, configured to perform the actions of the operations described above. In some implementations, the operations may be instructions that are encoded on a computer storage device.

These and other versions may each optionally include one or more of the following features. For instance, in some implementations, the first set of risk-scoring components may represent physical attributes related to the entity.

In some implementations, the second set of risk-scoring components represent behavioral attributes related to the entity.

According to another innovative aspect of the present disclosure, a method performed by a data processing apparatus for generating a set of training data that is used to improve the performance of a machine learning model used to predict a risk-level associated with an entity is disclosed. The method may include actions of obtaining, from one or more databases, a profile of attributes related to an entity, segmenting the obtained profile of attributes into distinct sets of risk-scoring components, with the segmenting based on a risk-type that is associated with each respective attribute, wherein the distinct sets of risk-scoring components include at least a first set of risk-scoring components and a second set of risk-scoring components, and wherein each respective attribute is segmented into only one of the first set of risk-scoring components or the second set of risk-scoring components, mapping each of the risk-scoring components of the first set of risk-scoring components to one or more categories of a first plurality of categories, mapping each of the risk-scoring components of the second set of risk-scoring components to one or more categories of a second plurality of categories, and generating a training data structure based on (i) the mapping of the first set of risk-scoring components, and (ii) the mapping of the second set of risk-scoring components.

Other versions include corresponding systems, apparatus, methods, and computer programs, configured to perform the actions of the operations described above. In some implementations, the operations may be instructions that are encoded on a computer storage device.

These and other versions may each optionally include one or more of the following features. For instance, in some implementations, the profile of attributes may include behavioral health attributes and physical health attributes. In such implementations, the method may further include segmenting the behavioral health attributes from the physical health attributes in quantifying health of a patient represented by the profile of attributes, and assigning, based on the segmented behavioral health attributes and the segmented physical health attributes, a health care coordinator to the patient, wherein segmentation of the behavioral health attributes from the physical health attributes in assigning the health care coordinator improves one or more patient outcomes, relative to patient outcomes independent of segmentation of the behavioral health attributes from the physical health attributes in assigning the health care coordinator.

In some implementations, mapping each of the risk-scoring components of the first set of risk-scoring components to one or more of the first plurality of categories may include identifying a set of one or more categories defined by a first model into which each of the first set of risk-scoring components is classified.

In some implementations, mapping each of the risk-scoring components of the second set of risk-scoring components to one or more of the second plurality of categories may include identifying a set of one or more categories defined by a second model into which each of the second set of risk-scoring components is classified.

In some implementations, generating the training data structure based on the (i) segmented first set of risk-scoring components, and the (ii) segmented second set of risk-scoring components may include generating a training feature vector that represents features corresponding to each category of the first model and each category of the second model.

In some implementations, the method may further include, for each feature of the training feature vector, assigning a first value to the feature if a risk-scoring component is mapped to the category to which the feature corresponds, and assigning a second value that is different than the first value to the feature if a risk-scoring component cannot be mapped to the category from which the feature is derived.

In some implementations, the training feature vector may also include one or more features representing demographic information related to the entity.

In some implementations, the first set of risk-scoring components may represent physical attributes related to the entity.

In some implementations, the second set of risk-scoring component may represent behavioral attributes related to the entity.

DETAILED DESCRIPTION

According to one innovative aspect of the present disclosure, a method for training a machine learning model to predict entity risk.

This specification describes how a system implemented as computer programs on one or more computers in one or more locations generates a set of training data structures (e.g., structured data with a plurality of fields for training a model, with each field storing a value for the training) or training data records that can be used to train a machine learning model to predict entity risk-levels. The trained model can then be used to process a set of features about an entity and predict a risk-level associated with the entity. The output of the trained model can be used to take one or more corrective actions based on the risk-level associated with the entity.

The training data structures generated by the present disclosure include a plurality of flexible data structures that each represent a feature vector of a training sample. Each feature vector is representative of multiple features derived from a training sample. The training sample may include, for example, an entity profile. The training data structures are flexible because each respective training data structure may be assigned a weight representing each respective feature of the feature vector. Thus, each training data structure of the plurality of training data structures can be particularly configured to cause certain inferences to be made by a machine learning model during training. As a result, the novel training data structures that are generated in accordance with this specification are designed to improve the performance of a machine learning model because they can be used to train a machine learning model to predict entity risk. That is, a machine learning model that could not perform entity risk-level predictions prior to being trained using the training data structures generated by this disclosure can learn to make entity risk-level predictions by being trained using the training data structures generated by the present disclosure. This process takes an otherwise general purpose machine learning model and changes the general purpose machine leaning model into a specific computer for perform a specific task of performing entity risk-level predictions.

The subject matter of the present disclosure provides other advantages separate from improving a machine learning model so that the machine learning model can perform entity risk-level predictions. For example, the subject matter of the present disclosure provides a real health benefit. By way of example, entity outcomes and the assignment of care coordinators to entities can each be improved based on the segmentation of entity profiles into physical health categories and behavioral health categories.

Figure 1:
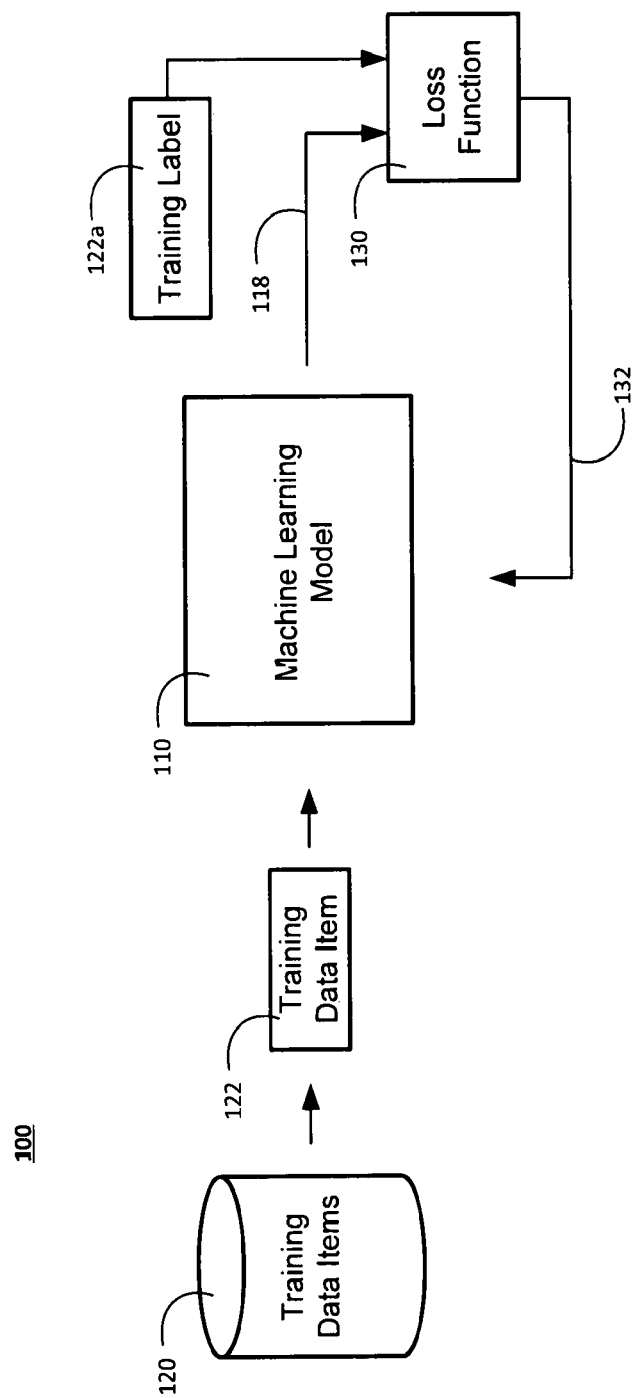
FIG. 1 is a block diagram of an example of a system for training a machine learning model.

FIG. 1 is a block diagram of an example of a system 100 for training a machine learning model 110. In some implementations, the machine learning model may be, for example, a support vector machine. Alternatively, the machine learning model may include a neural network, a linear regression machine learning model, or the like. The machine learning model training system 100 may be implemented as computer programs on one or more computers in one or more locations, in which the systems, components, and techniques described below can be implemented. The machine learning model training system 100 trains the machine learning model 110 using training data structure from a database (or data set) 120 of training data structures. The training data structures may include a plurality of feature vectors. Each training vector may include a plurality of values that each correspond to a particular feature of training sample that the training vector represents. The training features may be referred to as independent variables. In addition, the system 100 maintains a respective weight for each feature that is included in the feature vectors.

The machine learning model 110 is configured to receive an input training data structure 122 and to process the input training data structure 122 to generate an output. The input training data structure may include a plurality of features (or independent variables "X") and a training label (or dependent variable "Y"). The machine learning model may be trained using the training items, and once trained, is capable of predicting $X=f(Y)$.

To enable machine learning model 110 to generate accurate outputs for received data items, the machine learning model training system 100 may train the machine learning model 110 to adjust the values of the parameters in a parameter vector of the machine learning model 110, e.g., to determine trained values of the parameters from initial values. These parameters derived from the training steps may include weights that can be used to during the prediction stage using the fully trained machine learning model 110.

In training, the machine learning model 110, the machine learning model training system 100 uses training data structures stored in the database (data set) 120 of labeled training data structures. The database 120 stores a set of multiple training data structures, with each training data structure in the set of multiple training items being associated with a respective label. Generally, the label for the training data structure identities a correct classification (or prediction) for the training data structure, i.e., the classification that should be identified as the classification of the training data structure by the output values generated by the machine learning model 110. With reference to FIG. 1, a training data structure 122 may be associated with a training label 122a.

The machine learning model training system 100 trains the machine learning model 110 to optimize an objective function. Optimizing an objective function may include, for example, minimizing a loss function 130. Generally, the loss function 130 is a function that depends on the (i) output 118 generated by the machine learning model 110 by processing a given training data structure 122 and (ii) the label 122a for the training data structure 122, i.e., the target output that the machine learning model 110 should have generated by processing the training data structure 122.

The machine learning model training system 100 can train the machine learning model 110 to minimize the (cumulative) loss function 130 by performing multiple iterations of machine learning model training techniques on training data structures from the database 120 such as hinge loss, stochastic gradient methods, stochastic gradient descent with backpropagation, or the like, to iteratively adjust the values of the parameters of the machine learning model 110. A fully trained machine learning model 110 may be then be deployed as a predicting model that can be used to make predictions based on input data that is not labeled.

Figure 2:
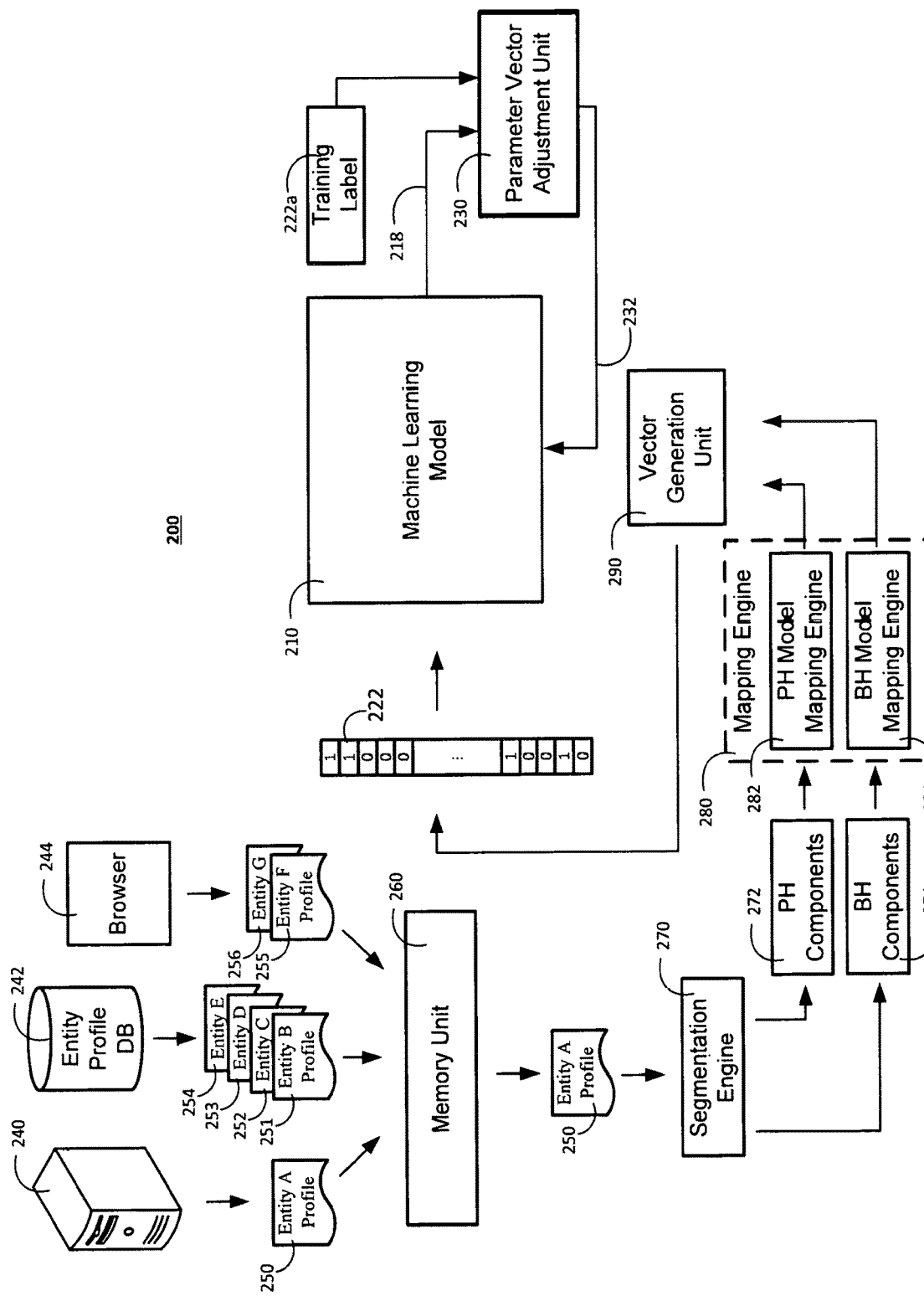
FIG. 2 is a block diagram of a system that generates training data for training a machine learning model to identify entity risk.

FIG. 2 is a block diagram of a system 200 that generates training data for training a machine learning model 210 to identify entity risk. The system 200 includes a machine learning model 210, a parameter vector adjustment unit 230, a plurality of training data sources 240, 242, 244, a memory unit 260, a segmentation engine 270, a model mapping engine 272, and a vector generation unit 290. In some implementations, the machine learning model 210 may include a vector support machine.

The machine learning model 210, the parameter vector adjustment unit 230, the memory unit 260, the segmentation engine 270, the model mapping engine 272, and the vector generation unit 290 may each be housed by one or more computing devices such as one or more server computers. In some implementations, one or more of the machine learning model 210, parameter vector adjustment unit 230, the segmentation engine 270, the model mapping engine 272, and the vector generation unit 290 may be comprised of software components that stored on one or more memory devices of the one or more computing devices. The memory devices storing one or more of the machine learning model 210, parameter vector adjustment unit 230, the segmentation engine 270, the model mapping engine 272, and the vector generation unit 290 may include a shared (e.g., semiconductor) memory, which can reduce latency in performing the data processing operations described herein, as compared with the latency that would be experienced if the aforementioned components of system 200 were stored on a hard disk.

In some implementations, each of the machine learning model 210, parameter vector adjustment unit 230, the segmentation engine 270, the model mapping engine 272, and the vector generation unit 290 may be stored on separate computing devices. In other implementations, each of the machine learning model 210, parameter vector adjustment unit 230, the segmentation engine 270, the model mapping engine 272, and the vector generation unit 290 may be stored on the same computing device. In other implementations, a single computing device may include two more of the machine learning model 210, parameter vector adjustment unit 230, the segmentation engine 270, the model mapping engine 272, and the vector generation unit 290 while one or more of the machine learning model 210, parameter vector adjustment unit 230, the segmentation engine 270, the model mapping engine 272, and the vector generation unit 290 are stored on another computing device.

Each of the machine learning model 210, parameter vector adjustment unit 230, the segmentation engine 270, the model mapping engine 272, and the vector generation unit 290 may include one or more executable logic engines comprise programmed logic that, when executed, performs the operations described as being performed by the machine learning model 210, parameter vector adjustment unit 230, the segmentation engine 270, the model mapping engine 272, and the vector generation unit 290 herein. Alternatively, the system 200 may include one or more executable logic engines may also be configured to obtain outputs from one component of the system 200, provide the obtained output to an input of another component of the system 200, and trigger the performance of one or more operations at the other component of the system 200. Accordingly, multiple executable logic engines comprising computer programmed logic, when executed by one or more processors, can work together achieve programmed functionality that implements the operations described as being performed by the system 200.

One or more computing devices storing at least one of the aforementioned machine learning model 210, parameter vector adjustment unit 230, the segmentation engine 270, the model mapping engine 272, the vector generation unit 290, or a combination thereof, may include an input port or input device that is configured to receive training data structures from one or more other components of system 200 and provide the received training data structures to the machine learning model 210 for processing. The input port may include a network interface port, PCI port, communications bus, or a combination thereof, or any other interface and set of interconnections that facilitate receipt of one or more training data structures and communication of the training data structures to the machine learning model 210. In some implementations, an input device may include, for example, a memory device storing a software module corresponding to the machine learning model 210, parameter vector adjustment unit 230, the segmentation engine 270, the model mapping engine 272, or the vector generation unit 290. For example, machine learning model 210 may include programmed functionality that, when executed by one or more processors of a computing device, enables the machine learning model 210 to receive one or more training data structures.

In some implementations, the shared memory storing one or more of the machine learning model 210, parameter vector adjustment unit 230, the segmentation engine 270, the model mapping engine 272, and the vector generation unit 290 may include the memory 260. By way of example, the shared memory may store the machine learning model 210, including one or more parameter vector data structures that define a current state of the machine learning model. In other implementations, the shared memory storing one or more of the machine learning model 210, parameter vector adjustment unit 230, the segmentation engine 270, the model mapping engine 272, and the vector generation unit 290 may be a different shared (e.g., semi-conductor) memory other than the memory 260.

Each of the plurality of training data sources 240, 242, 244 can store, provide, or both, training data structures that relate to respective entities for use in training the machine learning model 210. The training data sources 240, 242, 244 may provide training data structures to a memory unit 260 via one or input ports or input devices of a computing device that includes the memory unit 260. The input ports or input devices may include, for example, include a network interface port, PCI port, communications bus, or a combination thereof, or any other interface and set of interconnections that facilitate receipt of one or more training data structures and communication of the training data structures to the memory unit 260. In some implementations, the training data structures provided may include data representing one or more entity profiles such as entity profiles 250, 251, 252, 253, 254, 255, 256 each describing one or more attributes about the entity. In some implementations, the attributes may include data representing one or more medical conditions of an entity. The plurality of training data sources 240, 242, 244 may provide the training data in a variety of different ways.

For example, the training data source 240 can store, provide, or both, data representing one or more entity profiles 250 in real-time from one or more computers to the memory unit 260 of system 200 via one or more networks. The one or more networks may include a LAN, a WAN, the cellular network, the Internet, or the like. The system 200 may achieve efficiency gains by storing the entity profiles 250 received in real-time in memory as opposed to storing the entity profiles received in real-time in a database such as entity profile database 242. Gains in efficiency can be achieved because the memory unit 160 is faster than the database storage. In some implementations, for example, the memory unit 160 may use an in-memory data grid to store entity profiles received in real-time. In addition, storing the received real-time training data in memory unit 160 avoids the steps of writing the training data structure from training data source 240 to the database 242 and then later retrieving the training data structure from the database 242 so that the training data structure can be provided to the segmentation engine 270. For purposes of this disclosure, providing data in real-time may include real-time or near real-time.

By way of another example, the training data source 244 can store, provide, or both, training data structures such as data representing entity profiles 255, 256 in real-time via a browser installed on a computer to the memory unit 260 via one or more networks. In some implementations, due to technical limitations on the size of data that can be transmitted through a browser, the training data source 244 can convert the entity profiles 256, 257 to bitmap format and provide the entity profile 256, 257 in real-time to the memory unit 260. The system 200 can achieve additional efficiency gains by receiving and storing the entity profiles 256, 257 in bitmap format. In addition, the system 200 can continue to operate on the entity profiles 256, 257 in bitmap format until a vector is generated based on the received entity profiles 256, 257. As a result, not only does the system 200 gain efficiencies by using the memory unit 260, the in-memory data grid, or both, as described above to store received entity profiles in real-time without use of a database such as a data warehouse, but the system 200 also achieves efficiency gains by using the bitmap format for entity profiles received from a browser.

By way of another example, the system 200 can also obtain batches of training data structures such as data representing entity profiles 251, 252, 253, 254 from a database such as entity profile database 242. Such a system provides the advantage of obtaining large volumes of training data structures such as large volumes of entity profiles. The database may include, for example, a data warehouse. In some implementations, the system 200 can load a batch of entity profiles from the entity profile database and store the batch of entity profiles in the memory unit 260, the in-memory data grid of the memory unit 160, or both. Moving the batch of entity profiles from the entity profile database 242 to the memory unit 160 for storage in an in-memory data grid will increase the performance of the system 200 by reducing the time that it would to individually identify, access, and retrieve each respective entity profile from the entity profile database.

Each respective training data structure such as entity profile 250 stored in the memory unit 160, in-memory data grid, or both, may be provided as an input to a segmentation engine 270. The segmentation engine 270 is configured to obtain attributes from a received entity profile 250 and segment the attributes into distinct sets of risk-scoring components based on attribute type. A risk-scoring component is data describing the attribute that can be input into the mapping engine and mapped to one or more categories of a model. By way of example, the segmentation engine 270 may be configured to segment the attributes into first set of risk-scoring components and a second set of risk-scoring components. Each respective set of risk-scoring components may include a group of risk-scoring components based on attributes of the user profile. In some implementations, any particular user attribute may only be segmented into a single set of risk-scoring components.

In some implementations, such as the example of FIG. 2, entity attributes may correspond to entity attributes corresponding to one or more medical conditions related to a particular entity. Such medical conditions may be related to physical health conditions or behavioral health conditions. In such implementations, the segmentation engine 270 is configured to segment the attributes related to physical health conditions into the first set of risk-scoring components 272 and the attributes related to physical health conditions into the second set of risk scoring components 274. The first set of risk-storing components 272 representing the physical health conditions of an entity and the second set of risk-scoring components 274 representing the behavioral health conditions of the entity may be provided as an input to the mapping engine 280.

In some implementations, the system 200 may use the output of the segmentation engine 270 to identify a health care coordinator to the patient. Assigning, based on the segmented behavioral health attributes and the segmented physical health attributes, a health care coordinator to the patient, wherein segmentation of the behavioral health attributes from the physical health attributes in assigning the health care coordinator improves one or more patient outcomes, relative to patient outcomes independent of segmentation of the behavioral health attributes from the physical health attributes in assigning the health care coordinator.

The mapping engine 280 is configured to determine whether each risk-scoring component corresponds to a particular category of one or more models. In some implementations, such as the example of FIG. 2, the mapping engine 280 may include a plurality of mapping engines such as physical health model mapping engine 282 and a behavioral model mapping engine 284. Each respective mapping engine 282, 285 may be associated with a respective model. For example, the physical health mapping engine 282 may be associated with a physical health model and the behavioral health mapping engine 284 may be associated with a behavioral health model. Each respective model may be configured to receive a risk-scoring component and determine whether the risk-scoring component maps to a particular category of the model.

By way of example, the physical health model mapping engine 282 may be configured to receive the segmented set of physical health risk scoring components 272. The physical health model mapping engine 282 can derive information about an entity's medical history based on the entity's respective physical health risk-scoring components. Then, the physical health model mapping engine 282 may determine whether the derived information corresponds to one or more categories of the physical health model. The physical health model may include a plurality of categories associated with a person's physical health including, for example, chest, heart, or the like. In one implementation, the physical health model may include the Chronic Illness and Disability Payment System (CDPS) model. Alternatively, in another implementation, the system 200 may use a modified CDPS model that has had each of its behavioral health categories removed. In such implementations, the removed behavioral health categories can be added to the behavioral health model used by the system 200. Use of the modified CDPS model ensures a greater degree of diversity between physical health categories and the behavioral health categories. The output of the physical health model mapping engine 282 may include a mapping of physical health risk-scoring components 272 to physical health categories. For example, the output of the physical health model mapping engine 272 may include data describing which categories of the physical health model that the user's physical health risk-scoring components map to.

Similarly, the behavioral health model mapping engine 282 may be configured to receive the segmented set of behavioral health risk scoring components 274. The behavioral health model mapping engine 284 can drive information about an entity's medical history based on the entity's behavioral health risk-scoring components. Then, the behavioral health model mapping engine 282 may determine whether the derived information corresponds to one or more categories of a behavioral health model. They behavioral health model may include a plurality of behavioral health categories including, for example, addition to smoking, alcohol abuse, or the like. In some implementations, the behavioral health model used by the system 200 may incorporate the behavioral health categories removed from the CDPS model. The output of the behavioral health model mapping engine 284 may include a mapping of behavioral health risk-scoring components 274 to behavioral health categories. For example, the output of the behavioral health mapping engine may include data describing which categories of the behavioral health model that the user's behavioral health risk-scoring components map to.

The respective outputs of the mapping engine 280 may be provided as an input to the vector generation unit 290. The vector generation unit 290 is used to generate a data structure based on the outputs of the mapping engine 280. The generated data structure is a feature vector that includes a plurality of values that numerically represent the output of the mapping engine 280 in a feature vector space. For example, the feature vector may indicate which categories of the respective models that the entity's risk-scoring components map to. By way of example, the feature vector may include a field that corresponds to each category of the respective model. That is a field for each physical health category and a field for each behavioral health category. The vector generation unit 290 may assign numerical values to each respective field that indicates whether or not an entity's respective risk-scoring components map to the respective field. In one implementation, for example, the vector generation unit 290 may assign a '1' to each field of the feature vector that corresponds to a physical health category or a behavioral health category that the user's risk scoring components map to. In such implementations, the vector generation unit 290 may, for example, also assign a '0' to each field of the feature vector that corresponds to a physical health category or a behavioral health category that the user's respective risk-scoring components do not map to. In some implementations, a feature vector generated by the vector generation unit 290 may also include demographic information such as age, gender, or the like describing the entity represented by the feature vector 222.

The output of the vector generation unit 290 may include a training data structures such as a feature vector 222 that can be used to train the machine learning model 210. For example, an executable logic engine can obtain, or receive, a training data structure such as feature vector 222 that is output by the vector generation unit 290 and then provide the generated training data structure such as feature vector 222 as an input to the machine learning model 210. The executable logic engine may be part of vector generation unit 290, part of the machine learning model 210, or software or hardware module that is independent of both the vector generation unit 290 and the machine learning model 210.

The system 200 can label the training feature vector 222. The label of the training feature vector 222 may be a risk-value associated with the entity represented by the feature vector 222. The risk-value may include a historical cost associated with the entity's health care costs.

The system 200 can train the machine learning model 210 by providing the feature vector 222 as an input to the machine learning model 210. The machine learning model 210 may process the generated feature vector 222 and generate an output 218.

The generated output 218 is then provided to a parameter vector adjustment engine 230. For example, in some implementations, the same executable logic engine described above, or a different executable logic engine than the executable logic engine described above, can capture a data, or data structure, that is generated as an output 218 by the machine learning model 210 and provide the data, or data structure, generated as an output 218 by the machine learning model 210 based on the machine learning model's 210 processing of a training data structure such as the generated feature vector 222. The executable logic engine that captures the data, or data structure, generated as an output 218 by the machine learning model 210 based on the processing of the part of the machine learning model 210, the parameter vector adjustment engine 230, or a software or hardware module that is independent of the machine learning model 210 and the parameter vector adjustment engine 230.

The parameter vector adjustment engine 230 may be configured to parse the data structure input into the machine learning model by the executable logic engine to identify a field storing a first value representing a risk level. In some implementations, the first value may correspond to a label that is associated with the generated feature vector 222. In other implementations, the first value may be any risk level associated with the generated feature vector 222 and not an assigned label. The parameter vector adjustment engine 230 may be further configured to parse the output data 218, or data structure, generated by the machine learning model 210 based on the machine learning model's 210 processing of an input data structure such as the feature vector 222 to identify a field in the output data 218, data structure, storing a second value representing an output risk-level output from the machine learning model.

The parameter vector adjustment engine 230 is also configured to an amount error between the labeled risk value of the input training data structure such as the generated feature vector 222 and the output data 218 generated as output data 218, or data structure, by the machine learning model 210 based on the machine learning model's 210 processing of the training data structure such as feature vector 222. Determining an amount of error may include, for example, determining an amount of error between the second value output from the machine learning model and the first value of the risk-level of the data structure. In some implementations, this can be done in a number of ways such as by using one or more loss functions that calculate the error between the input feature vector 222 input into the machine learning model 210 and the output data 218 generated by the machine learning model 210 based on the processing of the input feature vector 222.

The parameter adjustment engine 230 is also configured to access an entry in the parameter vector data structure of the machine learning model that stores a vector (or matrix) one or more parameters of the machine learning model and adjust the one or more parameter values of the machine learning model based on the determined amount of error. In some implementations that have been optimized to reduce data processing latency, the parameter adjustment engine 230 can access one or more machine learning model 210 parameters stored in a shared (e.g., semi-conductor) memory and then update the parameters stored in the shared memory based on the determined amount of error. This parameter adjustment technique may be iteratively performed for different sets of input training data structures until the determined loss between one or more values of an input training data structure such as a labeled risk value and the output generated by the machine learning model's processing of the input training data structure satisfies a predetermined error threshold.

The system 200 may perform the process described above with reference to FIG. 2 for each training data structure such as entity profiles 251, 252, 253, 254, 255, 256 to generate training feature vectors that are used to train the machine learning model 210 to predict entity risk levels.

Figure 3:
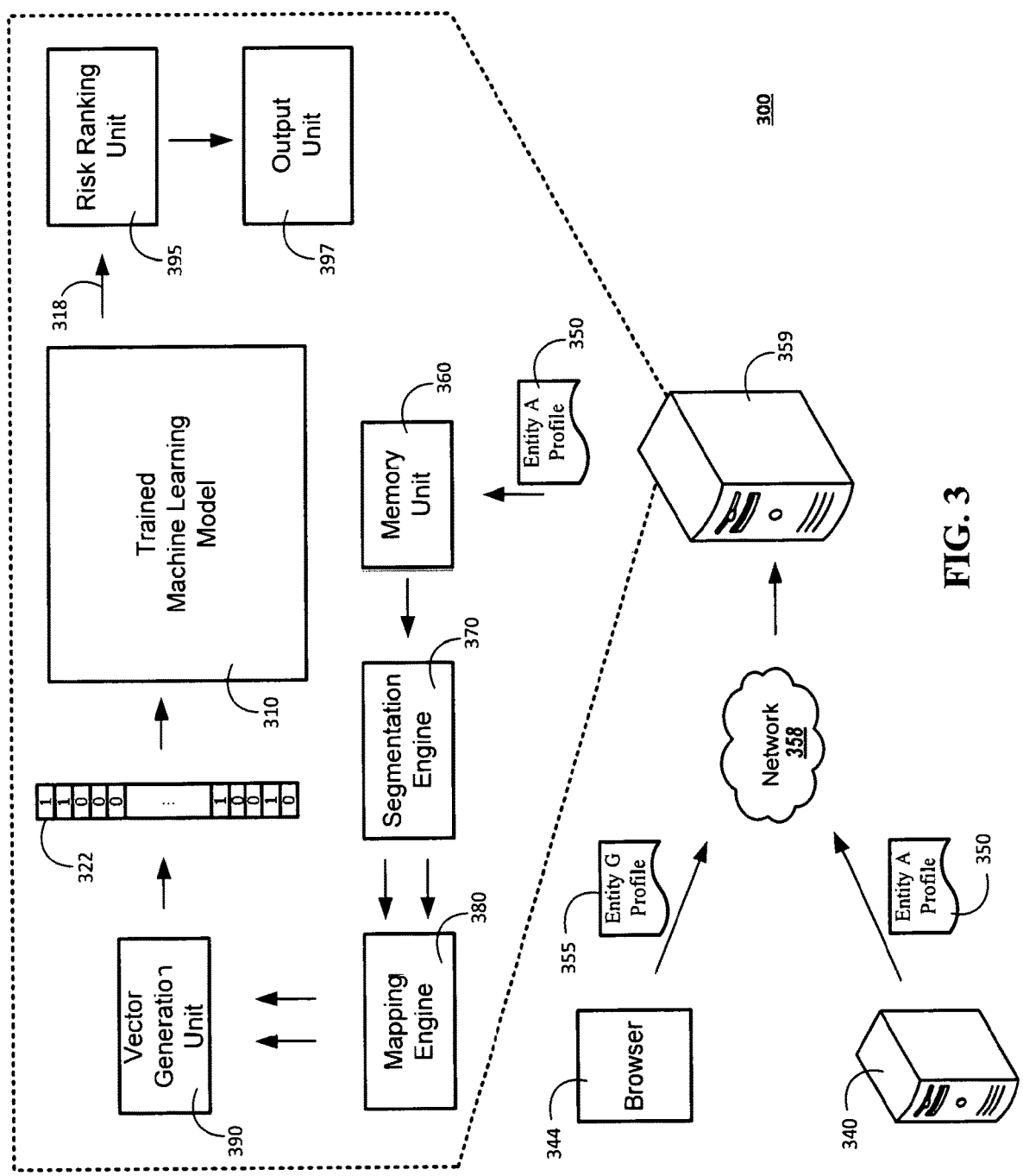
FIG. 3 is a block diagram of a system for using a machine learning model that has been trained to identify entity risk to rank entities.

FIG. 3 is a block diagram of a system 300 for using a machine learning model 310 that has been trained to identify entity risk to rank entities.

The machine learning model 310 includes a machine learning model that has been trained using the process described with reference to the system of FIG. 2. The trained machine learning model is capable of predicting, based on an input feature vector representative of the physical health categories and behavioral health categories associated with an entity's medical history.

The server 359 hosting the machine learning model 310 may receive one or more data records representing unlabeled entity profiles 350, 355 from one or more sources 340, 344 in real-time and store the unlabeled entity profiles 350, 355 in memory 360. Hereinafter, data records representing "unlabeled entity profiles" may be referred to herein as unlabeled entity profiles, for purposes of convenience and without limitation. In some implementations, memory 360 is selected to minimize the performance impact of writing data records. For example, it can be advantageous to reduce latency introduced by writing the data records to memory 360. In some implementations, memory 360 may be shared memory 360. Operations which write to shared (e.g., semi-conductor) memory generally introduce less overhead and are consequently faster than similar operations writing to a persistent data store, such as a magnetic disk. In some implementations, such as when the one or more unlabeled entity profiles 355 is the received from a browser, the unlabeled entity profile 355 may be received in bitmap form and stored in memory 360 in bitmap format. The unlabeled entity profiles 350, 355 may be received in real-time and stored in the memory unit 360. The server 359 may process each respective unlabeled entity profile to generate a feature vector 322.

For example, the server 350 may obtain each respective entity profile such as entity profile A 350 from the memory unit 360. In some implementations, server 359 may obtain the entity profile 350 from an in-memory data grid and provide each respective unlabeled entity profile such as entity profile 350 to the segmentation engine 370.

The segmentation engine 370 may perform the same operations on the unlabeled entity profile 350 as described with respect to segmentation engine 270 above. For example, the segmentation engine 370 may segment attributes identified in the entity profile 350 into one or more sets of risk-score components. By way of example, the entity profile 350 may include one or more attributes related to the medical record of an entity. The segmentation engine 370 may segment the attributes into a plurality of sets of risk-score components. For example, the segmentation engine may segment the one or more attributes of the entity's medical record into a physical health risk-score components and behavior health risk-score components. The segmentation engine 370 may provide the set of physical health risk-score components and the set of behavioral health risk-score components to the mapping engine 380.

The mapping engine 380 may perform the same operations on first set of physical health risk-score components and behavioral health risk-score components as described with respect to the mapping engine 380. For example, the mapping engine 370 may map each risk-score component to a particular category of a physical health model or a particular category of a behavioral health model. The output of the mapping engine may be provided to the vector generation unit 390.

The vector generation unit 390 can generate a feature vector 322 that includes a plurality of fields that each correspond to a physical health category or behavioral health category. The feature vector generation unit 390 may assign first value such as '1' to each respective field of the feature vector 322 if the entity profile included an attribute that corresponds to a physical health category or a behavioral health category included in the feature vector 322. Alternatively, the feature vector generation unit 390 may assign a different second value such as '0' to each respective field of the feature vector 322 if the entity profile did not include an attribute that corresponds to a physical health category or a behavior health category. In some implementations, the feature vector 322 may also include features corresponding to the entity's demographics such as age, gender, or the like.

The trained machine learning model 310 process the generated feature vector 322 based on the adjusted parameters that were determining during the training stage. The output 318 is predicted risk-value that the machine learning model determines based on a function of the generated feature vector 322 and the adjusted parameters of the machine learning model developed during the training stage. The trained machine learning model 310 may perform this operation of processing a generated feature vector and outputting a predicted risk-value for the entity for each respective entity profile received by the server 359.

The server 359 may use a risk ranking unit 395 to rank the risk-value for each respective entity. The ranking of risk-values for each respective entity provides allows for the identification of entities at varying portions of the risk-spectrum. For example, using the ranking of risk-values, the server 300 can identify the entity that is associated with the most risk, the entity that is associated with the least risk, a median risk-value for a population of entities, or the like. The risk ranking unit 395 can output lists of entities that are ranked based on predicted risk-values using the output unit 397.

Alternatively, or in addition, the risk-ranking unit 395 may monitor newly predicted risk-values in order to identify entities that are associated with a high risk-value. In some implementations, for example, the ranking unit 395 can determine whether each predicted risk-value satisfies a predetermined threshold. If the predicted risk-value for an entity exceeds a predetermined risk-value, the server 359 can providing an instruction to the output unit 397 to notify a user of the system 300 that a high-risk entity has been identified.

Figure 4:
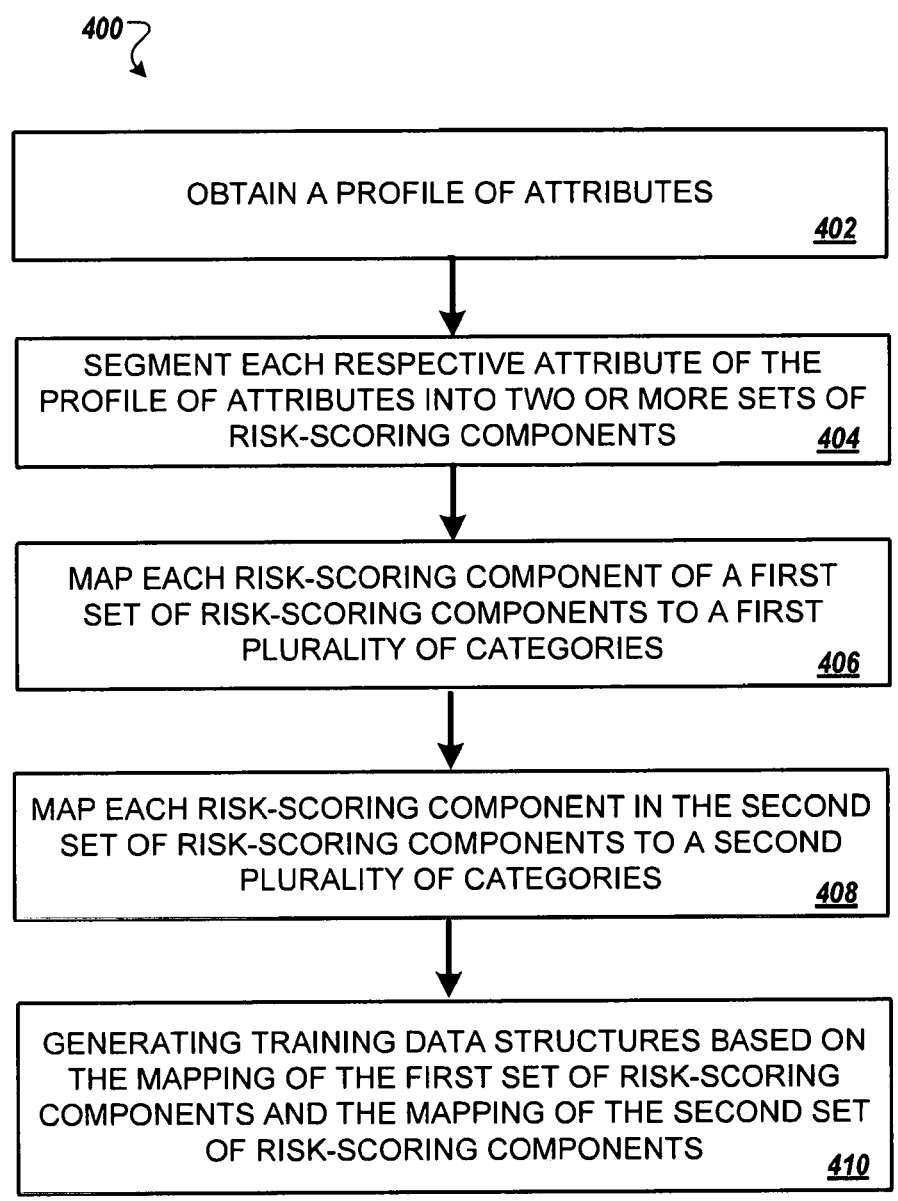
FIG. 4 is a flowchart of a process for generating training data for training a machine learning model to identify entity risk.

FIG. 4 is a flowchart of a process 400 for generating training data for training a machine learning model to identify entity risk. Generally, the process 400 includes obtaining a profile of attributes (402), segmenting each respective attribute of the profile of attributes into one or more sets of risk-scoring components (404), mapping each risk-scoring component of a first set of risk scoring components to a first plurality of categories (406), mapping each risk-scoring component in the second set of risk-scoring components to a second plurality of categories (408), and generating training data structures based on the mapping of the first set of risk-scoring components and the mapping of the second set of risk-scoring components (410). For convenience, the process 400 will be described below as being performed by a system such as system 200.

The system can begins performance of the process 400 by obtaining 410 a profile of attributes: In some implementations, obtaining the profile of attributes may include receiving the profile of attributes, in real-time, from one or more remote computers and stored in a main memory of the system. Alternatively, obtaining the profile of attributes may include obtaining the profile of attributes from the main memory of the system. The profile of attributes may include, for example, a plurality of attributes about an entity. The entity may include a person. The attributes may include data describing the person's medical history.

The system can segment 404 each respective attribute of the profile of attributes into two or more sets of risk-scoring components. The two or more sets of risk-scoring components may include first group of risk-scoring components that is distinct from the second group of risk-scoring components. In one implementation, any attribute included in one of the sets of risk-scoring components cannot be included in another set of risk-scoring components. In one implementations, the attributes may be segmented into a first group of physical health attributes and a second group of behavioral health attributes.

The system can map 406 each risk-scoring component of a first set of risk-scoring components to a first plurality of categories. The first plurality of categories may be defined by a first model. In some implementations, the first model may include a physical health model that defines a plurality of physical health categories. The mapping of each risk-scoring component of the first set of risk-scoring components to a physical health categories of a physical health model results in the generation of data that indicates whether the entity is associated with one or more attributes corresponding to one or more respective physical health categories.

The system can map 408 each risk-scoring component of a second set of risk-scoring components to a second plurality of categories. The second plurality of categories may be defined by a second model. The second model may be different than the first model. In some implementations, the second model may include a behavioral health model that defines a plurality of behavioral health categories. The mapping of each risk-scoring component of the second set of risk-scoring components to a behavioral health categories of a behavioral health model results in the generation of data that indicates whether the entity is associated with one or more attributes corresponding to one or more respective behavioral health categories.

The system can generate 410 training data structures based on the mapping of the first set of risk-scoring components and the mapping of the second set of risk-scoring components. The generated training data structure may include a feature vector. The feature vector may include a plurality of features that each correspond to one respective category of the first plurality of categories or the second plurality of categories. Generating the training data structure may include, for example, assigning numerical values to each respective field that indicates whether or not an entity's respective risk-scoring components map to the respective field. In one implementation, for example, the system may assign a '1' to each field of the feature vector that corresponds to a physical health category or a behavioral health category that the user's respective risk-scoring components map to. In such implementations, the system may, for example, also assign a different values such as a '0' to each field of the feature vector that corresponds to a physical health category or a behavioral health category that the user's risk scoring components do not map to.

In some implementations, generating the training data structure may also include labeling the training data structures. Labeling the training data structures includes associating a value with the training data structure that should be generated as an output of the machine learning model when the machine learning model processes the training data structure as an input.

Figure 5:
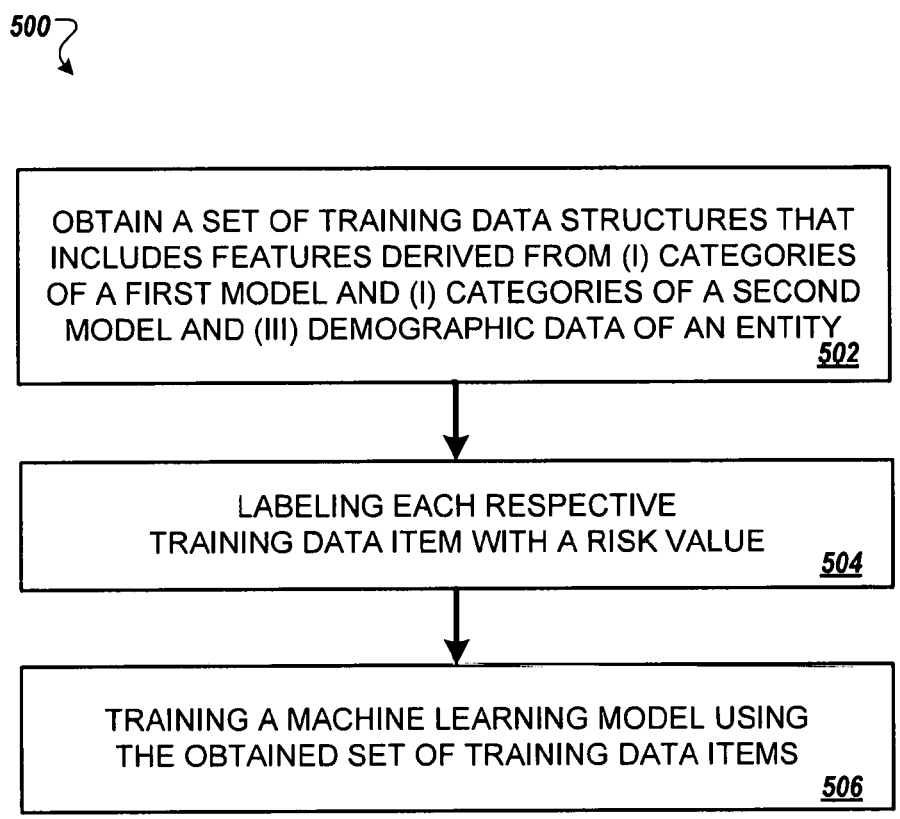
FIG. 5 is a flowchart of a process for training a machine learning model to identify entity risk.

FIG. 5 is a flowchart of a process 500 for training a machine learning model to identify entity risk. Generally, the process 500 includes generating a set of training data structures that includes features derived from (i) categories of a first model and (ii) categories of a second model and (iii) demographic data of an entity (502), labeling each respective training data structure with a risk value (504), and training a machine learning model using the obtained set of training data structures (506). For convenience, the process 500 will be described below as being performed by a system such as a system 200.

A system may begin the process 500 by obtaining 502 a set of training data structures that includes features derived from (i) categories of a first model, (ii) categories of a second model, and (iii) demographic data of an entity. The training data structure may include a training feature vector. The features derived from categories of the first model may include features that correspond to one or more physical health category of a physical health model. The features derived from the categories of the second model may include features that correspond to one or more behavioral health categories of a behavioral health model. The features derived from the demographic data of an entity may include, for example, the entity's age, gender, or the like.

The system can label 504 each respective training data structure with a risk value. Alternatively, in other implementations, the training data structures obtained at stage 502 already be associated with a risk value label. The risk value may include, for example, data describing the entity's medical history.

The system can train 506 a machine learning model using the obtained set of training data structures. Training the machine learning model may include providing the obtained training data structure as an input to the machine learning model. The machine learning model may process the obtained training data structure and generate an output. The system can use a loss function to determine the amount of error between the output of the machine learning model and the value specified by the training label. The output of the parameter vector adjustment unit 230 can be used to adjust the parameters of the machine learning model.

Figure 6:
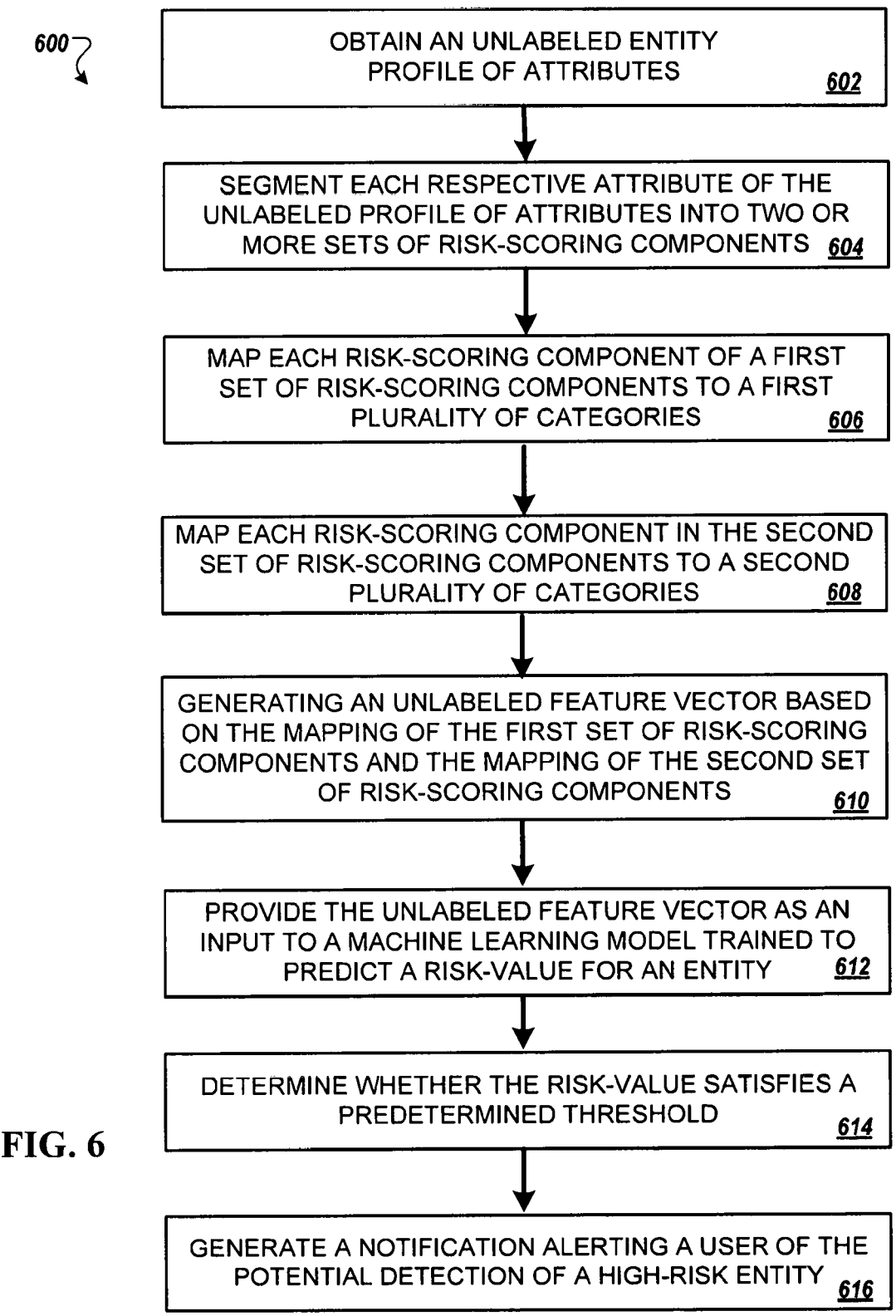
FIG. 6 is a flowchart of a process for using a machine learning model that has been trained to identify risk to rank entities.

FIG. 6 is a flowchart of a process 600 for using a machine learning model that has been trained to identify risk to rank entities. Generally, the process 600 include obtaining an unlabeled profile of attributes (602), segmenting each respective attribute of the profile of attributes into one or more sets of risk-scoring components (604), mapping each risk-scoring component of the plurality of risk-scoring components to a first plurality of categories (606), mapping each risk-scoring component in the second set of risk-scoring components to a second plurality of categories (608), generating an unlabeled feature vector based on (i) the mapping of the first set of risk-scoring components and (ii) the mapping of the second set of risk-scoring components (610), providing the unlabeled feature vector as an input to a machine learning model trained to predict a risk-value for an entity (612), determining whether the risk-value satisfies a predetermined threshold (612), and generating a notification alerting a user of the potential detection of a high-risk entity (614). The process 600 will be described as being performed below by a system such as a system 300.

The system can begin performance of the process 600 by obtaining 610 an unlabeled profile of attributes. The unlabeled profile of attributes may include real-time data associated with an entity that is not marked as being associated with a predetermined risk value. In some implementations, obtaining the unlabeled profile of attributes may include receiving the unlabeled profile of attributes, in real-time, from one or more remote computers and stored in a main memory of the system. Alternatively, obtaining the unlabeled profile of attributes may include obtaining the unlabeled profile of attributes from the main memory of the system. The unlabeled profile of attributes may include, for example, a plurality of attributes about an entity. The entity may include a person. The attributes may include data describing the person's medical history.

The system can segment 604 each respective attribute of the unlabeled profile of attributes into two or more sets of risk-scoring components. The two or more sets of risk-scoring components may include first group of risk-scoring components that is distinct from the second group of risk-scoring components. In one implementation, any attribute included in one of the sets of risk-scoring components cannot be included in another set of risk-scoring components. In one implementations, the attributes may be segmented into a first group of physical health attributes and a second group of behavioral health attributes.

The system can map 606 each risk-scoring component of a first set of risk-scoring components to a first plurality of categories. The first plurality of categories may be defined by a first model. In some implementations, the first model may include a physical health model that defines a plurality of physical health categories. The mapping of each risk-scoring component of the first set of risk-scoring components to a physical health categories of a physical health model results in the generation of data that indicates whether the entity is associated with one or more attributes corresponding to one or more respective physical health categories.

The system can map 608 each risk-scoring component of a second set of risk-scoring components to a second plurality of categories. The second plurality of categories may be defined by a second model. The second model may be different than the first model. In some implementations, the second model may include a behavioral health model that defines a plurality of behavioral health categories. The mapping of each risk-scoring component of the second set of risk-scoring components to a behavioral health categories of a behavioral health model results in the generation of data that indicates whether the entity is associated with one or more attributes corresponding to one or more respective behavioral health categories.

The system can generate 610 an unlabeled feature vector based on the mapping of the first set of risk-scoring components and the mapping of the second set of risk-scoring components. The unlabeled feature vector may include a plurality of features that each correspond to one respective category of a first plurality of categories or the second plurality of categories. Generating the unlabeled feature vector may include, for example, assigning numerical values to each respective field that indicates whether or not an entity's respective risk-scoring components map to the respective field. In one implementation, for example, the system may assign a '1' to each field of the feature vector that corresponds to a physical health category or a behavioral health category that the user's respective risk-scoring components map to. In such implementations, the system may, for example, also assign a different values such as a '0' to each field of the feature vector that corresponds to a physical health category or a behavioral health category that the user's risk scoring components do not map to.

The system can provide 612 the unlabeled feature vector as an input to a machine learning model that has been trained to predict a risk-value for the entity. In some implementations, the machine learning model may be trained to predict a risk-value for the entity using the process 500. The machine learning model may process the unlabeled feature vector as an input and generate an output that is representative of a predicted risk-value for the entity based on the input of the unlabeled feature vector.

The system can determine 614 whether the risk-value satisfies a predetermined threshold. In response to determining that the risk-value satisfies a predetermined threshold the system may generate 616 a notification alerting a user of the potential detection of a high-risk entity. Alternatively, if the system determines that the risk-value does not satisfy the predetermined threshold the system can determine to not alert the user. In some implementations, the risk-value may satisfy the predetermined threshold if the risk-value exceeds the predetermined threshold.

Aspects of the present disclosure may directed towards performing a cost trend analysis to identify entities that are associated with rising levels of risk. An entity may be associated with a rising level of risk if it is determined that the entity's healthcare costs are rising or likely to rise. In some implementations, a cost trend analysis may be performed using the MACD algorithm. The algorithm may include, for example, determining a long term moving average (e.g., 26 days), determining a short term moving average (e.g., 12 days), determining a MACD series (e.g., 12 days minus 26 days moving average (difference between 'fast' EMA and 'slow' EMA), determining a MACD signal line, (e.g., Moving average MACD (9 days) (Average series)), determining a divergence equal to the difference between the MACD series and the MACD signal line), determining a STD (e.g., standard deviation over presumably the entire time series), determining a Group STD (e.g., average STD of a matched cohort), for each time period, calculating how far away is 'divergence' at that time from mean divergence, identify divergence that is 5 or more Group STD away, and for the last 30 days, pick the last event that is 5 or more Group STD away, if any, for a user.

The system may be configured to extract data associated with entities whose health are likely going to be high. The determination of whether the respective entity has increased ER visits, hospital visits, or the like. Change in cost trends for an entity may be determined in response a recent uptick in the entities hospital usage, ER usage, or the like.

The system may be configured to predict return on investment values. For example, the system may compare health care provider's actual costs vs. the healthcare provider's predicted cost. The predictive cost may be applied at the provider level. The system may determine whether there are particular attributes that are predisposed to do better, or not.

Embodiments of the subject matter, the functional operations and the processes described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively, or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps may be provided, or steps may be eliminated, from the described processes. Accordingly, other implementations are within the scope of the following claims.

The invention claimed is:

1. A method performed by a data processing apparatus for training a machine learning model to improve the machine learning model's accuracy, the method comprising:

accessing, by a mapping engine, a plurality of risk scoring components associated with an entity;

mapping, by the mapping engine, a first set of risk scoring components, from among the plurality of risk scoring components, to one or more physical health categories based on a first model that recognizes risk scoring components as belonging to the one or more physical health categories;

mapping, by the mapping engine, a second set of risk scoring components, from among the plurality of risk scoring components, to one or more behavioral health categories based on a second model that recognizes the second set of risk scoring components as belonging to the one or more behavioral health categories;

generating a plurality of training data structures, wherein each training data structure includes (i) a plurality of first features derived from the first set of risk scoring components mapped to the one or more physical health categories by the first model and (ii) a plurality of second features derived from the second set of risk scoring components mapped to the one or more behavioral health categories by the second model, wherein generating the plurality of training data structures comprises:

generating a feature vector based on the plurality of first features and the plurality of second features, wherein the feature vector comprises a data field to indicate whether the feature is based on a risk scoring component that is mapped to the one or more physical health categories or is based on a risk scoring component that is mapped to the one or more behavioral health categories; and assigning, for each first feature from among the plurality of first features, a first value of the data field in the feature vector to indicate that a first corresponding risk scoring component is mapped to the one or more physical health categories;

assigning, for each second feature from among the plurality of second features, a second value of the data field in the feature vector to indicate that a second corresponding risk scoring component is mapped to the one or more behavioral health categories if the second corresponding risk scoring component cannot be mapped to the one or more physical health categories;

obtaining, for each training data structure, a target output;

providing the plurality of training data structures as an input to the machine learning model configured to predict, based on the physical health categories and the behavioral health categories, a risk-level associated with an entity;

determining an amount of error between the predicted risk-level associated with the entity outputted by the machine learning model and the target output of the plurality of training data structures; and retraining, based on the determined amount of error, the machine learning model after adjusting one or more parameters of the machine learning model.

2. The method of claim 1, wherein the plurality of training data structure further comprises a diagnostic code.

3. The method of claim 1, wherein the plurality of training data structure further comprises a pharmacy code.

4. The method of claim 1, wherein the plurality of training data structure further comprises demographic information of the entity.

5. The method of claim 1, wherein the one or more physical health categories comprise categories related to a physical health of the entity.

6. The method of claim 1, wherein the one or more behavioral health categories comprise categories related to a behavioral health of the entity.

7. The method of claim 1, wherein the risk-level associated with the entity represents a historical health care cost associated with the entity.

8. A system comprising one or more computers and one or more storage devices storing instructions that are operable, when executed by one or more computers, to cause the one or more computers to:

access a plurality of risk scoring components associated with an entity;

map a first set of risk scoring components, from among the plurality of risk scoring components, to one or more physical health categories based on a first model that recognizes risk scoring components as belonging to the one or more physical health categories;

map a second set of risk scoring components, from among the plurality of risk scoring components, to one or more behavioral health categories based on a second model that recognizes the second set of risk scoring components as belonging to the one or more behavioral health categories;

generate a plurality of training data structures, wherein each training data structure includes (i) a plurality of first features derived from the first set of risk scoring components mapped to the one or more physical health categories by the first model and (ii) a plurality of second features derived from the second set of risk scoring components mapped to the one or more behavioral health categories by the second model, wherein to generate the plurality of training data structures, the one or more computers are caused to:

generate a feature vector based on the plurality of first features and the plurality of second features, wherein the feature vector comprises a data field to indicate whether the feature is based on a risk scoring component that is mapped to the one or more physical health categories or is based on a risk scoring component that is mapped to the one or more behavioral health categories;

assign, for each first feature from among the plurality of first features, a first value of the data field in the feature vector to indicate that a first corresponding risk scoring component is mapped to the one or more physical health categories;

assign, for each second feature from among the plurality of second features, a second value of the data field in the feature vector to indicate that a second corresponding risk scoring component is mapped to the one or more behavioral health categories if the second corresponding risk scoring component cannot be mapped to the one or more physical health categories;

obtain, for each training data structure, a target output;

provide the plurality of training data structures as an input to a machine learning model configured to predict, based on the physical health categories and the behavioral health categories, a risk-level associated with an entity;

determine an amount of error between the predicted risk-level associated with the entity outputted by the machine learning model and the target output of the plurality of training data structures; and retrain, based on the determined amount of error, the machine learning model after adjusting one or more parameters of the machine learning model.

9. The system of claim 8, wherein the plurality of training data structure further comprises a diagnostic code.

10. The system of claim 8, wherein the plurality of training data structure further comprises a pharmacy code.

11. The system of claim 8, wherein the plurality of training data structure further comprises demographic information of the entity.

12. The system of claim 8, wherein the one or more physical health categories comprise categories related to a physical health of the entity.

13. The system of claim 8, wherein the one or more behavioral health categories comprise categories related to a behavioral health of the entity.

14. The system of claim 8, wherein the risk-level associated with the entity represents a historical health care cost associated with the entity.

15. A non-transitory computer storage medium encoded with instructions that, when executed by one or more computers, cause the one or more computers to:

access a plurality of risk scoring components associated with an entity;

map a first set of risk scoring components, from among the plurality of risk scoring components, to one or more physical health categories based on a first model that recognizes risk scoring components as belonging to the one or more physical health categories;

map a second set of risk scoring components, from among the plurality of risk scoring components, to one or more behavioral health categories based on a second model that recognizes the second set of risk scoring components as belonging to the one or more behavioral health categories;

generate a plurality of training data structures, wherein each training data structure includes (i) a plurality of first features derived from the first set of risk scoring components mapped to the one or more physical health categories by the first model and (ii) a plurality of second features derived from the second set of risk scoring components mapped to the one or more behavioral health categories by the second model, wherein to generate the plurality of training data structures, the one or more computers are caused to:

generate a feature vector based on the plurality of first features and the plurality of second features, wherein the feature vector comprises a data field to indicate whether the feature is based on a risk scoring component that is mapped to the one or more physical health categories or is based on a risk scoring component that is mapped to the one or more behavioral health categories;

assign, for each first feature from among the plurality of first features, a first value of the data field in the feature vector to indicate that a first corresponding risk scoring component is mapped to the one or more physical health categories;

assign, for each second feature from among the plurality of second features, a second value of the data field in the feature vector to indicate that a second corresponding risk scoring component is mapped to the one or more behavioral health categories if the second corresponding risk scoring component cannot be mapped to the one or more physical health categories;

obtain, for each training data structure, a target output;

provide, the plurality of training data structures as an input to a machine learning model configured to predict, based on the physical health categories and the behavioral health categories, a risk-level associated with an entity;

determine an amount of error between the predicted risk-level associated with the entity outputted by the machine learning model and the target output of the plurality of training data structures; and retrain, based on the determined amount of error, the machine learning model after adjusting one or more parameters of the machine learning model.

16. The non-transitory computer storage medium of claim 15, wherein the plurality of training data structure further comprises a diagnostic code.

17. The non-transitory computer storage medium of claim 15, wherein the plurality of training data structure further comprises a pharmacy code.

18. The non-transitory computer storage medium of claim 15, wherein the plurality of training data structure further comprises demographic information of the entity.

19. The non-transitory computer storage medium of claim 15, wherein the one or more physical health categories comprise categories related to a physical health of the entity.

20. The non-transitory computer storage medium of claim 15, wherein the one or more behavioral health categories comprise categories related to a behavioral health of the entity.

21. The non-transitory computer storage medium of claim 15, wherein the risk-level associated with the entity represents a historical health care cost associated with the entity.

22. The non-transitory computer storage medium of claim 15, wherein each feature of the plurality of first and second features is assigned a first value if the one or more risk scoring components can be mapped to the category from which the feature is derived.

23. The non-transitory computer storage medium of claim 15, wherein each feature of the plurality of first and second features is assigned a second value that is different from the first value if the one or more risk scoring components cannot be mapped to the category from which the feature is derived.

* * * * *